United States Patent [19]

Boguslaski et al.

[11] 4,355,165
[45] Oct. 19, 1982

[54] AMINO-FUNCTIONALIZED PHTHALHYDRAZIDE INTERMEDIATES

[75] Inventors: Robert C. Boguslaski; Robert J. Carrico, both of Elkhart, Ind.; James E. Christner, Birmingham, Ala.

[73] Assignee: Miles Laboratories, Inc., Elkhart, Ind.

[21] Appl. No.: 131,881

[22] Filed: Mar. 20, 1980

Related U.S. Application Data

[60] Division of Ser. No. 927,622, Jul. 24, 1978, which is a continuation-in-part of Ser. No. 894,836, Apr. 10, 1978, which is a continuation of Ser. No. 667,996, Mar. 18, 1976, abandoned, which is a continuation-in-part of Ser. No. 572,008, Apr. 28, 1975, abandoned.

[51] Int. Cl.³ .......................................... C07D 237/32
[52] U.S. Cl. ..................................... 544/237; 424/250
[58] Field of Search ............................... 544/237, 235

[56] References Cited

U.S. PATENT DOCUMENTS

| | | | |
|---|---|---|---|
| 4,096,143 | 6/1978 | Sato et al. | 544/237 |
| 4,104,029 | 8/1978 | Maier | 260/230 B |
| 4,226,992 | 10/1980 | Buckler et al. | 544/234 |

FOREIGN PATENT DOCUMENTS 1100911  1/1968  United Kingdom .

Primary Examiner—Nicholas S. Rizzo
Attorney, Agent, or Firm—Andrew L. Klawitter

[57] ABSTRACT

Amino-functionalized phthalhydrazide intermediates of the formula:

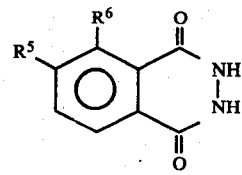

wherein one of $R^5$ and $R^6$ is hydrogen and the other is $-NR^7R^8$; $R^7$ is hydrogen or straight chain alkyl containing 1-4 carbon atoms and $R^8$ is

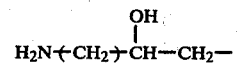

wherein n=1-3. The compounds are intermediates in the synthesis of chemiluminescent-labeled conjugates which are useful as reagents in specific binding assays for determining ligands or their specific binding partners in liquid media.

5 Claims, No Drawings

AMINO-FUNCTIONALIZED PHTHALHYDRAZIDE INTERMEDIATES

CROSS-REFERENCE TO RELATED APPLICATIONS

This is a division of application Ser. No. 927,622, filed July 24, 1978, which is a continuation-in-part of application Ser. No. 894,836, filed Apr. 10, 1978; which is a continuation of application Ser. No. 667,996, filed Mar. 18, 1976, now abandoned; which is a continuation-in-part of application Ser. No. 572,008, filed Apr. 28, 1975, now abandoned.

BACKGROUND OF THE INVENTION

1. Field of the Invention

This invention relates to novel chemiluminescent-labeled conjugates for use in specific binding assays for a ligand, such as an antigen, hapten or antibody, in a liquid medium such as a body fluid. The invention further relates to intermediate compounds produced in the synthesis of the novel labeled conjugates.

The desirability of a convenient, reliable, and nonhazardous means for detecting the presence of low concentrations of substances in liquids is self-evident. This is particularly true in the field of clinical chemistry where constituents of body fluids which may appear in concentrations as low as $10^{-11}$ molar are known to be of pathological significance. The difficulty of detecting such low concentrations is compounded in the field of clinical chemistry where sample size is usually quite limited.

Classically, substances have been detected in liquids based on a reaction scheme wherein the substance to be detected is a necessary reactant. The presence of unknown is indicated by the appearance of a reaction product or the disappearance of a known reactant. In certain instances, such an assay method may be quantitative, based on a measurement of either the rate of appearance of product or disappearance of reactant or measurement of the aggregate amount of product produced or reactant consumed in attaining equilibrium. Each assay reaction system is necessarily either limited to use in the detection of only a small group of substances or is nonspecific.

The search for assay systems which are highly specific yet adaptable to the detection of a wide range of substances has evolved the radioimmunoassay. In this system a known amount of a radiolabeled form of the substance to be detected is allowed to compete with the unknown for a limited quantity of antibody specific for the unknown. The amount of the labeled form that becomes bound to antibody varies inversely with the level of unknown present. Inherent in the radioimmunoassay technique is the need to separate the labeled form of substance to be detected which becomes bound to antibody from that which does not become so bound. While various ways of accomplishing the required separation have been developed, as exemplified in U.S. Pat. Nos. 3,505,019; 3,555,143; 3,646,346; 3,720,760; and 3,793,445, all require at least one separate manipulative step, such as filtering, centrifuging, or washing, to insure efficient separation of the bound-labeled form from the unbound-labeled form. The elimination of the separation step would greatly simplify the assay and render it more useful to the clinical laboratory.

The use of radioactive materials in immunoassays has been eliminated to some degree by the use of enzyme-tagged materials in place of radiolabels. As exemplified by U.S. Pat. Nos. 3,654,090 and 3,791,932, the manipulative steps necessary for carrying out the enzyme-tagged immunoassays are for the most part the same as those required in radioimmunoassays and include the cumbersome separation step. An additional disadvantage of using enzyme-tagged materials is that each enzyme used as a tag must be individually chemically modified for use in the formation of the tagged conjugate. The use of other tagging materials has been suggested, such as the use of coenzymes or viruses, Nature 219:186(1968) and the use of fluorescent labels, French Pat. No. 2,217,350 corresponding to U.S. Pat. No. 3,880,934.

2. Brief Description of the Prior Art

While these radiolabeled and enzyme-tagged immunoassays may undergo future improvement in terms of expansion of the range of substances detectable thereby or of simplification of the procedure, by their nature they will always require some type of separation step. Recently, a different approach was disclosed which does not require a separation step and therefore has been referred to as a homogeneous system, in contrast to a heterogeneous system in which separation is essential. U.S. Pat. No. 3,817,837 discloses a competitive binding assay method involving the steps of combining the liquid to be assayed with a soluble complex consisting of an enzyme as a labeling substance covalently bound to the ligand to be detected and with a soluble receptor, usually an antibody, for the ligand; and analyzing for the effect of the liquid to be assayed on the enzymatic activity of the enzyme in the complex.

While this method has the advantage of not requiring a separation step because reaction between the enzyme-bound-ligand complex and the receptor results in inhibition of the enzymatic activity of the enzyme in the complex, the method nonetheless is severely restricted in its ability to be adapted to widely varied assay requirements. For instance, it is clearly essential that in the fabrication of the enzyme-bound-ligand complex, the substance or ligand to be detected must be coupled to the enzyme in a carefully controlled manner so that the coupling site is close to the enzymatically active site on the enzyme. This is required in order that upon reaction between the complexed ligand and the receptor, the enzymatically active site is blocked. Enzymes vary greatly in their size, ranging in molecular weight from about 10,000 to 1,000,000. Thus, for a receptor in the form of an antibody having a molecular weight of between 150,000 and 300,000 to be capable of physically blocking the active site on an average enzyme of 500,000 molecular weight or greater, the coupling site must be precisely controlled. Due to the complex chemical structure of enzymes, precise control of such chemical linkage is indeed difficult, and one would expect that even upon screening a wide variety of enzymes only a small number would be found to be of use in this homogeneous assay system.

Moreover, it is critical for the purpose of obtaining quantitative test results to precisely control the ratio of the number of enzymes to the number of ligands in each enzyme-bound-ligand complex. Here also, the complex peptide structure of enzymes makes such control difficult. It would again be expected that only a small number of enzymes would have suitable molecular structure to ensure necessary control of the ligand/enzyme ratio.

The prior art homogeneous assay method is stated to involve an enzyme amplification and thus to be highly sensitive. However, since the labeling substance, namely the enzyme, is itself the limiting factor determining the sentitivity of the prior art assay method, the versatility of the method is severely restricted. The sensitivity is clearly limited to the catalytic activity of the particular enzyme in the enzyme-bound-ligand conjugate. The versatility of the prior art method is therefore restricted not only by the coupling requirements for formation of a useful conjugate but also by the dependence of the sensitivity of the assay that employs such conjugate on the activity of the particular conjugated enzyme.

An additional disadvantage of the prior art homogeneous assay method arises in its application to the testing of biological fluids, such as urine and serum. It is to be expected that significant amounts of the enzyme species comprised in the enzyme-bound-ligand conjugate may appear in the fluid sample to be tested thereby creating an uncontrollable background activity which would severely affect the accuracy of the assay method. Therefore, in order to form an assay system that is useable in testing biological fluids of humans or animals, exotic enzymes not endogenous to such fluids must be selected for use in forming the enzyme-bound-ligand conjugate with the result that the versatility of the assay method is even further restricted.

It is therefore an object of the present invention to provide a novel test composition, device, and method for detecting a ligand in a liquid which do not require a separation step and which do not employ inconvenient radioactive materials or modified enzymes as the labeling substance.

Further, it is an object of the present invention to provide a homogeneous specific binding assay method and system which are more versatile and convenient than those of the prior art.

Another object of the present invention is to provide a homogeneous specific binding assay method and system which employ a labeling substance which is capable of being coupled to the ligand or to a specific binding partner thereof more conveniently than can the enzyme of the prior art method.

A further object of the present invention is to provide a homogeneous specific binding assay method and system which employ a conjugate comprising a labeling substance whose activity is more readily affected by a specific binding reaction than is the enzyme of the prior art method.

It is also an object of the present invention to provide a homogeneous specific binding assay method and system which employ a conjugate comprising a labeling substance any change in the activity of which is more conveniently detectable using a wide variety of sensitive reaction systems than is any change in the activity of the enzyme in the prior art method.

It is a further object of the present invention to provide a homogeneous specific assay method and system which are more readily applicable to the testing of biological fluids than those of the prior art.

SUMMARY OF THE INVENTION

A highly convenient, versatile, and sensitive homogeneous specific binding assay method and system have now been devised based on the use of, as labeling substance, a substance which exhibits given reactant activity as a constituent of a predetermined reaction, such substance being referred to herein as the reactant. The method is based, in part, on the fact that the reaction between a ligand and a specific binding partner thereof to one of which the reactant is coupled alters the activity of the reactant in the predetermined reaction, which reaction thus serves as means for monitoring the specific binding reaction. In view of this basic phenomenon, various manipulative schemes involving various test compositions and devices may be employed in performing the method of the present invention. The preferred fundamental manipulative schemes are the direct binding technique and the competitive binding technique.

In the direct binding technique, a liquid medium suspected of containing the ligand to be detected is contacted with a conjugate comprising the reactant coupled to a specific binding partner of the ligand, and thereafter any change in the activity of the reactant is assessed. In the competitive binding technique, the liquid medium is contacted with a specific binding partner of the ligand and with a conjugate comprising the reactant coupled to one or both of the ligand or a specific binding analog thereof, and thereafter any change in the activity of the reactant is assessed. In both techniques, the activity of the reactant is determined by contacting the liquid medium with at least one reagent which forms, with the reactant, the predetermined monitoring reaction. Qualitative determination of the ligand in the liquid medium involves comparing a characteristic, usually the rate, of the resulting reaction to that of the monitoring reaction in a liquid medium devoid of the ligand, any difference therebetween being an indication of a change in activity of the reactant. Quantitative determination of the ligand in the liquid medium involves comparing a characteristic of the resulting reaction to that of the monitoring reaction in liquid media containing known amounts of the ligand.

The present invention relates particularly to a preferred monitoring reaction for the reactant-labeled specific binding assay method. Such monitoring reaction is based on chemiluminescence and comprises employing as the labeling substance in the conjugate a reactant in a chemiluminescent reaction to generate light and measuring the light produced either as total light produced or peak light intensity.

DESCRIPTION OF THE PREFERRED EMBODIMENTS

In the context of this disclosure, the following terms shall be defined as follows: ligand is the substance, or group of substances, whose presence or the amount thereof in a liquid medium is to be determined; specific binding partner of the ligand is any substance, or group of substances, which has a specific binding affinity for the ligand to the exclusion of other substances; and specific binding analog of the ligand is any substance, or group of substances, which behaves essentially the same as the ligand with respect to the binding affinity of the specific binding partner for the ligand.

In general, the components of the specific binding reaction, i.e., the liquid medium suspected of containing the ligand, the conjugate, and/or a specific binding partner of the ligand, may be combined in any amount, manner, and sequence, provided that the activity of the reactant in the conjugate is measurably altered when the liquid medium contains the ligand in an amount or concentration of significance to the purposes of the assay. Preferably, all of the components of the specific binding reaction are soluble in the liquid medium, thus providing a homogeneous assay system. However, a heterogeneous assay system wherein the conjugate or a specific binding partner of the ligand is insoluble may be employed if desired.

Where a direct binding technique is used, the components of the specific binding reaction are the liquid medium suspected of containing the ligand and a quantity of a conjugate comprising the reactant coupled to a specific binding partner of the ligand. The activity of the conjugated reactant on contact with the liquid medium varies inversely with the extent of binding between the ligand in the liquid medium and the specific binding partner in the conjugate. Thus, as the amount of ligand in the liquid medium increases, the activity of the conjugated reactant decreases. To obtain quantitative results, the amount of the specific binding partner contacted with the liquid medium is usually in excess of that capable of binding with all of the ligand thought to be present in the liquid medium during the time that the conjugate and the liquid medium are in contact prior to completion of the assessment of any change in activity of the conjugated reactant. In practice, an amount of the specific binding partner is chosen according to the above-mentioned criterion based on an estimation of the largest amount of the ligand which is likely to be present in the liquid medium. A direct binding technique is particularly useful in detecting high molecular weight ligands which have specific binding partners that are smaller than themselves.

Where a competitive binding technique is used, the components of the specific binding reaction are the liquid medium suspected of containing the ligand, a quantity of a conjugate comprising the reactant coupled to the ligand or a specific binding analog of the ligand, and a quantity of a specific binding partner of the ligand. The specific binding partner is contacted substantially simultaneously with both the conjugate and the liquid medium. Since any ligand in the liquid medium competes with the ligand or specific binding analog thereof in the conjugate for binding with the specific binding partner, the activity of the conjugated reactant on contact with the liquid medium varies directly with the extent of binding between the ligand in the liquid medium and the specific binding partner. Thus, as the amount of the ligand in the liquid medium increases, the activity of the conjugated reactant increases. To obtain quantitative results, the amount of the specific binding partner contacted with the conjugate and the liquid medium is usually less than that capable of binding with all of the ligand thought to be present in the liquid medium and all of the ligand or ligand analog in conjugated form in the time that the specific binding partner, the conjugate, and the liquid medium are in contact prior to completion of the assessment of any change in activity of the conjugated reactant. In practice, an amount of the specific binding partner is chosen according to the above-mentioned criterion based on an estimation of the largest amount of the ligand which is likely to be present in the liquid medium. Usually, the amount of the ligand or ligand analog in conjugated form which is contacted with the liquid medium does not exceed the smallest amount of the ligand to be tested for in the liquid medium. A competitive binding technique is particularly useful in detecting ligands which have specific binding partners that are larger than themselves.

A variation of the competitive binding technique is the displacement binding technique wherein the conjugate is contacted first with the specific binding partner of the ligand and thereafter with the liquid medium. Competition for the specific binding partner then occurs. In such a method, the amount of the conjugate contacted with the specific binding partner is usually that which comprises the ligand or analog thereof in excess of that capable of binding with the amount of the specific binding partner present during the time that the conjugate and the specific binding partner are in contact prior to contact with the liquid medium suspected of containing the ligand. This order of contact may be accomplished in either of two convenient ways. In one method, the conjugate is contacted with the specific binding partner in a liquid environment prior to contact with the liquid medium suspected of containing the ligand. In the second method, the liquid medium suspected of containing the ligand is contacted with a complex comprising the conjugate and the specific binding partner, the specific binding substance in the conjugate and the specific binding partner being reversibly bound to each other. The amount of the conjugate that becomes bound to the specific binding partner in the first method, as well as the amount thereof which is in complexed form in the second method, is usually in excess of that capable of being displaced by all of the ligand in the liquid medium in the time that the specific binding partner, or complex, and the medium are in contact prior to the completion of the assessment of any change in the activity of the conjugated reactant.

Another variation of the competitive binding technique is the sequential saturation technique wherein the components of the specific binding reaction are the same as those used in the competitive binding technique, but the order of addition or combination of the components and the relative amounts thereof used are different. Following a sequential saturation technique, the specific binding partner of the ligand is contacted with the liquid medium suspected of containing the ligand for a period of time prior to the contact of said liquid medium with the conjugate. The amount of the specific binding partner contacted with the liquid medium is usually in excess of that capable of binding with all of the ligand thought to be present in the liquid medium in the time that the specific binding partner and the liquid medium are in contact prior to the time that the liquid medium is contacted with the conjugate. Further, the amount of the ligand or ligand analog in conjugated form is usually in excess of that capable of binding with the remaining unbound amount of the specific binding partner during the time that the liquid medium and the conjugate are in contact prior to the completion of the assessment of any change in activity of the conjugated reactant. In practice, the amounts of the specific binding partner and of the ligand or ligand analog in conjugated form are chosen according to the above-mentioned criterion by estimating the largest amount of the ligand likely to be present in the liquid medium.

It is contemplated that manipulative schemes involving other orders of addition and other relative amounts of the specific binding reaction components may be devised for carrying out a homogeneous specific binding assay without departing from the inventive concept embodied herein.

The step of assessing any change in activity of the conjugated reactant as a constituent of the predetermined monitoring reaction is conveniently accomplished by contacting the specific binding reaction mixture with at least one substance which forms with the conjugated reactant, the monitoring reaction, and determining the effect of the specific binding reaction on a characteristic of such reaction. The monitoring reaction may comprise a single chemical transformation or a plurality or series of chemical transformations. Unless otherwise specified, the term "reaction system" as used herein refers to the whole or a portion of the predetermined monitoring reaction.

The appropriate reaction constituents which form, together with the reactant in the conjugate, the monitoring reaction may be contacted with the specific binding reaction mixture singularly or in any combination either prior to, simultaneous with, or subsequent to initiation of the specific binding reaction. After initiation of the specific binding reaction, the reaction mixture, which may include any or all of the necessary components for the monitoring reaction is usually incubated for a predetermined period of time before assessing any change in the activity of the reactant in the conjugate. After the incubation period, any components which are necessary for the monitoring reaction and which are not already present in sufficient quantities in the reaction mixture are added thereto, and any effect on the monitoring reaction is assessed as an indication of the presence or amount of the ligand in the liquid medium.

In the situation where the ligand is absent from the liquid medium, or is present in an insignificantly small amount, the predetermined monitoring reaction exhibits a relatively constant character. When the ligand is present in the liquid medium, at least one characteristic or property of the monitoring reaction is altered. Generally, the activity of the conjugated reactant is defined as the extent or rate at which the reactant is capable of participating in the monitoring reaction. Thus, the character of the monitoring reaction is altered by the presence of the ligand in the liquid medium, usually with respect to either the aggregate reaction rate thereof or the equilibrium quantity of one or more reaction products produced thereby. In the usual case, the ability of the conjugated reactant to participate in the monitoring reaction is decreased upon reaction between the specific binding substance to which it is conjugated and a specific binding counterpart of such specific binding substance, that is, the conjugate in its free state is more active in the monitoring reaction than in its bound state.

The relative amounts of free and bound conjugate present after the incubation of the specific binding reaction are a function of the amount of ligand in the liquid medium and are determinative of the effect on the monitoring reaction.

It will be recognized, of course, that in an instance where the reactant activity of the labeling substance in the labeled conjugate is not altered significantly by binding thereof in the binding reaction, a useful assay method results if the free- and bound-species of the labeled conjugate are separated as in conventional heterogeneous binding assays prior to measuring reactant activity in the monitoring reaction. For this purpose, any conventional heterogeneous technique can be used including competitive binding methods, sequential saturation methods, direct binding methods, and "sandwich" binding methods. Further details concerning the state of this art may be found in German Offenlegungsschrift No. 2,618,419.

One preferred form of the monitoring reaction includes a luminescent reaction system, preferably enzyme-catalyzed, such as a reaction exhibiting the phenomenon of bioluminescence or chemiluminescence. The reactant in the conjugate i.e., the label, may be a reactant in either the light-producing reaction or a reaction which is preliminary to an enzymatic or nonenzymatic luminescent reaction. Any change in the activity of the conjugated reactant resulting from the specific binding reaction causes a change in the rate of light production or in the total amount, peak intensity, or character of the light produced. A chemiluminescent label, of course, will be recognized as a moiety in a labeled conjugate which is capable of undergoing a change in chemical structure with the production of light. Examples of luminescent reaction systems are given in Table A in which the following abbreviations are used:

ATP: adenosine triphosphate
AMP: adenosine monophosphate
NAD: nicotinamide adenine dinucleotide
NADH: reduced nicotinamide adenine dinucleotide
FMN: flavin mononucleotide
$FMNH_2$: reduced flavin mononucleotide
$h\nu$: electromagnetic radiation, usually in the infrared, visible, or ultraviolet region

TABLE A

| | Luminescent Reaction System | Conjugated Reactant |
|---|---|---|
| A. | $ATP + \text{reduced luciferin} \xrightarrow{\text{luciferase (fire fly)}} h\nu + AMP + \text{oxidized luciferin}$ | ATP or reduced luciferin |
| B. | $FMNH_2 + \text{long-chain aldehyde} + O_2 \xrightarrow{\text{luciferase (P. fisheri)}}$ $h\nu + FMN + \text{long-chain acid} + H_2O$ | $FMNH_2$ or long-chain aldehyde |
| C. | (1) $NADH + FMN + H^\oplus \xrightarrow{\text{NADH dehydrogenase}} NAD + FMNH_2$ (2) $FMNH_2 + \text{long-chain aldehyde} + O_2 \xrightarrow{\text{luciferase (P. fisheri)}}$ $h\nu + FMN + \text{long-chain acid} + H_2O$ | NADH or FMN |
| D. | (1) $3',5'\text{-adenosine diphosphate} + \text{reduced luciferin sulfate} \xrightarrow{\text{sulfate transferase}}$ adenosine-3'-phosphate-5'-phosphosulfate + reduced luciferin (2) $\text{reduced lucifern} + O_2 \longrightarrow h\nu + \text{oxidized luciferin}$ | 3'5'-adenosine diphosphate or reduced luciferin |

TABLE A-continued

| Luminescent Reaction System | Conjugated Reactant |
|---|---|
| E. reduced luminol + $H_2O_2$ $\xrightarrow{\text{peroxidase*}}$ $h\nu$ + oxidized luminol + $H_2O$ | reduced luminol |
| F. reduced pyrogallol + $H_2O_2$ $\xrightarrow{\text{peroxidase*}}$ $h\nu$ + oxidized pyrogallol + $H_2O$ | reduced pyrogallol |
| G. reduced luminol + $O_2$ $\xrightarrow{\text{oxygenase}}$ $h\nu$ + oxidized luminol | reduced luminol |
| H. reduced pyrogallol + $O_2$ $\xrightarrow{\text{oxygenase}}$ $h\nu$ + oxidized pyrogallol | reduced pyrogallol |
| I. isoluminol + $H_2O_2$ $\xrightarrow{\text{lactoperoxidase}}$ $h\nu$ + aminophthalate + $N_2$ | isoluminol |
| J. isoluminol + $KO_2$ $\longrightarrow$ $h\nu$ + aminophthalate + $N_2$ | isoluminol |

*or catalase

Particularly useful oxidation systems for the chemiluminescent monitoring reaction wherein the label is luminol or isoluminol, or a derivative thereof, are hydrogen peroxide combined with any of the following catalysts, peroxidase (particularly microperoxidase), catalase, deuterohemin, hematin or ferricyamide ions; hypochlorite ions combined with cobalt ions; persulfate ions; potassium superoxide; periodate ions; hypoxanthine combined with xanthine oxidase; or potassium t-butoxide.

The preferred chemiluminescent labels are luminol, isoluminol, pyrogallol and luciferin, and chemiluminescent derivatives thereof. Further details and discussion concerning luminescent reaction systems which may be, used in the present method may be found in the following references:

J. Biol. Chem. 236:48(1961).
J. Amer. Chem. Soc. 89:3944(1967).
Cornier et al, Bioluminescence in Progress, ed. Johnson et al, Princeton University Press (New Jersey, 1966) pp. 363–84.
Kries, P. Purification and Properties of Renilla Luciferase, doctoral thesis University of Georgia (1967).
Am. J. Physiol. 41:454(1916).
Biol. Bull. 51:89(1926).
J. Biol. Chem. 243:4714(1968).

While unnecessary in the preferred embodiment of the present invention, it may be desirable to employ a heterogeneous assay technique even where the presence of the ligand in a liquid medium affects the activity of the conjugated reactant (label). Such a situation may present itself where a heterogeneous system offers particular convenience. Certain heterogeneous systems have the ability to increase the effective concentration of the ligand in the assay system, thus increasing sensitivity. An example of such a heterogeneous system is that which employs a column device containing an insoluble matrix comprising either the conjugate of the present invention or a specific binding partner of the ligand, depending on the particular manipulative format selected. All other heterogeneous assay methods employing radio-labeled or enzyme-tagged materials as a labeling substance may also be followed using the reactant of the present invention as the labeling substance.

In general, it is preferred that the conjugate comprise the reactant coupled to the smaller of the ligand and its selected specific binding partner. It is preferred to use a direct binding technique to detect the ligand where the molecular weight of the selected specific binding partner is about one-tenth that of the ligand or less. Thus, where the ligand to be detected is an antibody or a specific binding receptor, it is preferred to follow a direct binding technique wherein the conjugate comprises an enzymatic reactant coupled to an antigen or hapten to the antibody or a lower molecular weight binding partner of the receptor. Where the molecular weight of the selected binding partner is ten or more times larger than that of the ligand to be detected, as when an antigen, hapten, hormone, vitamin, metabolite or pharmacological agent is to be detected, it is particularly advantageous to employ a competitive binding or sequential saturation technique in which the conjugate comprises the reactant coupled to the smaller ligand.

In the conjugate of the present invention, the reactant is coupled or bound to a specific binding substance, which is the ligand, a specific binding analog of the ligand, or a specific binding partner of the ligand depending upon the assay scheme selected, such that a measurable amount of activity of the reactant is retained. The bond between the reactant and the specific binding substance is subtantially irreversible under the conditions of the assay.

The reactant may be directly coupled to the specific binding substance so that the molecular weight of the conjugate is less than or equal to the aggregate molecular weight of the reactant and the specific binding substance. Usually, however, the reactant and the specific binding substance are linked by a bridge or linking group comprising between 1 and 50, and preferably between 1 and 10, carbon atoms or heteroatoms such as nitrogen, oxygen, sulfur, phosphorus and so forth. Examples of a bridge group comprising a single atom would be a methylene group (one carbon atom) and an amino group (one heteroatom). The bridge group usually has a molecular weight not exceeding 1000 and preferably less than 200. The bridge group comprises a chain of carbon atoms or heteroatoms, or a combination of both, and is joined to the reactant and the specific binding substance, or active derivative thereof, by a connecting group usually in the form of an ester, amido, ether, thioester, thioether, acetal, methylene, or amino group.

Accordingly, the chemiluminescent-labeled conjugates of the present invention will have the formula:

Chemi—R—L wherein Chemi represents a moiety which is capable of undergoing a change in chemical structure with the production of light, R is a linking group as described previously, and L is a specifically bindable ligand or a binding analog thereof. As stated previously, such chemiluminescent moiety is preferably luminol, isoluminol, pyrogallol or luciferin, and preferably either of the first two usually coupled to the linking group through their respective amino groups.

The specifically bindable ligand or analog thereof in the present labeled conjugates, in terms of its chemical nature, usually is a protein, polypeptide, peptide, carbohydrate, glycoprotein, steroid, or other organic molecule for which a specific binding partner is obtainable. In functional terms, the ligand will usually be an antigen or an antibody thereto; a hapten or an antibody thereto; or a hormone, vitamin, or drug, or a receptor or binding substance therefor. Most commonly, the ligand is an immunologically-active polypeptide or protein of molecular weight between 1,000 and 4,000,000 such as an antigenic polypeptide or protein or an antibody; or is a hapten of molecular weight between 100 and 1,500.

Particularly useful chemiluminescent-labeled conjugates of the present invention are of the formula:

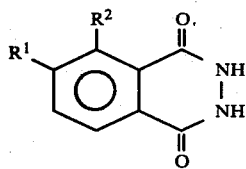

wherein one of $R^1$ and $R^2$, preferably $R^2$, is hydrogen and the other is $-NR^3R^4$; $R^3$ is hydrogen or straight chain alkyl containing 1-4 carbon atoms, preferably ethyl, and $R^4$ is

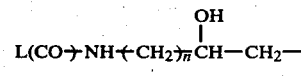

wherein n=1-3, preferably 1, and L(CO)- is a specifically bindable ligand, or a binding analog thereof, bound through an amide bond.

The present labeled conjugates are prepared usually by forming a peptide or amide couple between (1) an amino derivative of a chemiluminescent aminophthalhydrazide (e.g., luminol or isoluminol) and (2) either the ligand, where such contains a carboxylic acid function, or a binding analog of the ligand (e.g., a derivative of the ligand) which analog contains the desired carboxylic acid function. Such condensation reactions can be accomplished by reacting the amino derivative of the label directly with the carboxylic acid-containing ligand or ligand analog using conventional peptide condensation reactants such as the carbodiimide reaction [Science 144:1344(1964)], the mixed anhydride reaction [Erlanger, et al, *Methods In Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also for a general review *Clin. Chem.* 22:726(1976).

It will be recognized of course that other well known methods are available for coupling the ligand or a derivative thereof to the amino-derivative of the label. In particular, conventional bifunctional coupling agents may be employed for coupling a ligand, or its derivative, containing a carboxylic acid or amino group to the amino-derivative of the label. For example, amine-amine coupling agents such as bis-isocyanates, bis-imidoesters, and glutaraldehyde [*Immunochem.* 6:53(1969)] may be used to couple a ligand or derivative containing an amino group to the amino-derivative of the label. Also, appropriate coupling reactions are well known for inserting a bridge group in coupling an amine (e.g., the amino-derivative of the label) to a carboxylic acid (e.g., the ligand or a derivative thereof). Coupling reactions of this type are thoroughly discussed in the literature, for instance in the above-mentioned Kopple monograph and in Lowe & Dean, *Affinity Chromatography*, John Wiley & Sons (New York 1974).

Such coupling techniques will be considered equivalents to the previously discussed peptide condensation reactions in preparing useful labeled conjugates. The choice of coupling technique will depend on the functionalities available in the ligand or analog thereof for coupling to the label derivative and on the length of bridging group desired. In all cases, for purposes of this disclosure, the resulting labeled conjugate will comprise the label bound to the remaining portion of the conjugate through an amide bond. Such remaining portion of the conjugate will be considered as a residue of a binding analog of the ligand, unless the ligand itself is directly coupled to the label derivative. Thus, in this description and in the claims to follow, the abbreviation L(CO)- represents the ligand or a binding analog thereof coupled through an amide bond, wherein such analog may be a derivative of the ligand coupled by peptide condensation to the label derivative or may be the ligand or derivative thereof coupled through a bridging group inserted by coupling of the ligand or derivative to the label derivative with a bifunctional coupling agent.

Preparation of the present chemiluminescent-labeled conjugates proceeds according to the following general synthetic sequence:

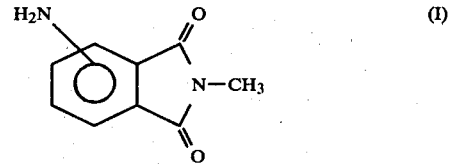

The starting material for the synthesis is 3- or 4-amino-N-methylphthalimide (I) with the 3-amino compound [Wang et al, JACS 72:4887(1950) and Flitsch, *Chem. Ber.* 94:2494(1961)] to be used to prepare luminol based labeled-conjugates and the 4-amino compound [Flitsch, *Chem. Ber.* 94:2494(1961)] to be used to prepare isoluminol based labeled-conjugates.

Alkylation of the amino group in the phthalimide (I) is obtained by reaction with a dialkyl sulfate (II) [Rodd, *Chemistry of Carbon Compounds*, vol. 1, Elsevier Publ. Co. (New York 1951) p. 337]

to yield the N-alkylated derivative (III)

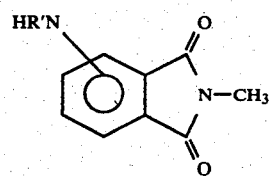
(III)

wherein R' is straight chain alkyl containing 1-4 carbon atoms.

Treatment of the phthalimide (I) or its N-alkylated derivative (III) with a chloro-epoxide (IV) [available from Aldrich Chemical Co., Milwaukee, Wisconsin USA, or see Paul et al, *Bull. Soc. Chim. Fr.* 197(1948) or Reppe, et al, *Justus Liebig's Annalen der Chemie* 596:80–158(1955)]

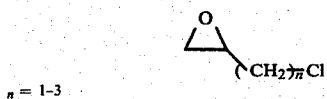
(IV)

produces the chloro-intermediate (V)

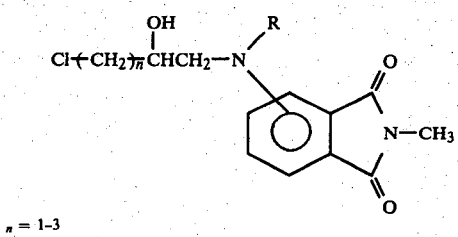
(V)

wherein R is hydrogen or straight chain alkyl containing 1-4 carbon atoms.

Reaction of the chloro-intermediate (V) with potassium phthalimide produces the bis-phthalimide intermediate (VI)

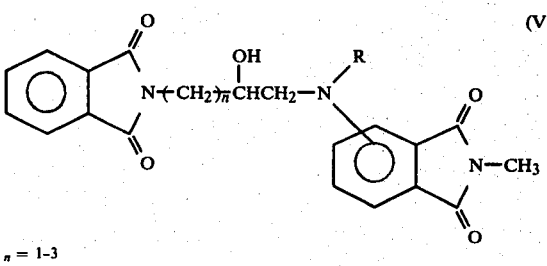
(VI)

wherein R is the same as defined above, which upon treatment with hydrazine produces the amino-hydrazide (VII)

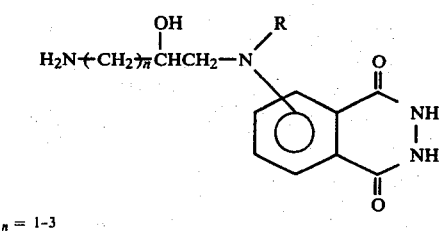
(VII)

wherein R again is the same as defined above.

Condensation of the amino-hydrazide (VII) with (a) the ligand to be labeled, where such contains a carboxylic acid function, (b) a binding analog of the ligand, such analog being a carboxylic acid derivative of the ligand, or (c) the ligand or an appropriate derivative of the ligand in the presence of a bifunctional coupling agent, produces the chemiluminescent-labeled conjugate (VIII)

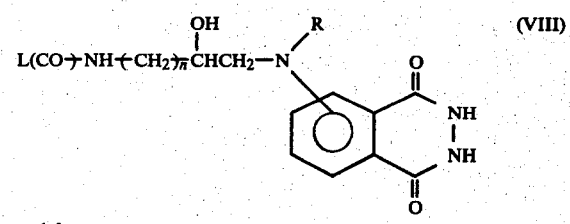
(VIII)

wherein R is the same as defined above and L(CO)— represents the specifically bindable ligand, or a binding analog thereof (formed by derivation of the ligand and/or insertion of a bridge by a bifunctional coupling agent), bound through an amide bond.

Other variations of labeled conjugate based on the above-described synthetic scheme are clearly evident. In particular, various ring-substituted amino-N-methylphthalimides may be used as starting material to produce ring-substituted labeled conjugates possessing substantially the same qualitative properties as the conjugates prepared according to the above-described scheme. Such conjugates will be recognized as equivalents and are exemplified by the addition of one, two or more simple substituents to an available aromatic ring site, such substituents including without limitation, alkyl, e.g., methyl, ethyl and butyl; halo, e.g., chloro and bromo; nitro, hydroxyl; alkoxy, e.g., methoxy and ethoxy, and so forth.

As illustrated in the above-described synthetic scheme, the novel intermediate compounds produced in the course of preparing the chemiluminescent-labeled conjugates have the following general formulae [the amino-hydrazides (VII) correspond to formula A below and the bis-phthalimides (VI) correspond to formula B below]:

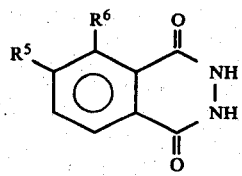
formula A wherein one of $R^5$ and $R^6$, preferably $R^6$, is hydrogen and the other is $-NR^7R^8$; $R^7$ is hydrogen or straight chain alkyl containing 1-4 carbon atoms, preferably ethyl, and $R^8$ is

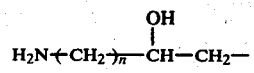

wherein n=1-3, preferably 1; and

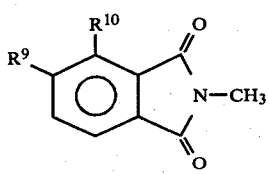

formula B wherein one of R⁹ and R¹⁰, preferably R¹⁰, is hydrogen and the other is —NR¹¹R¹²; R¹¹ is hydrogen or straight chain alkyl containing 1–4 carbon atoms, preferably ethyl; and R¹² is

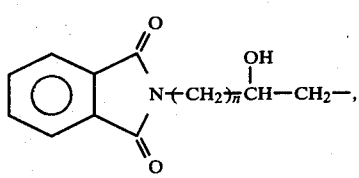

wherein n=1–3, preferably 1.

As stated hereinabove, the ligand which is comprised in the labeled conjugate or whose binding analog is comprised in the labeled conjugate is in most circumstances an immunologically-active polypeptide or protein of molecular weight between 1,000 and 4,000,000 such as an antigenic polypeptide or protein or an antibody; or is a hapten of molecular weight between 100 and 1,500. Following will now be presented various methods for coupling such ligands or analogs thereof to the amino-derivative (VII) of the label through an amide bond.

Polypeptides and Proteins

Representative of specifically bindable protein ligands are antibodies in general, particularly those of the IgG, IgE, IgM and IgA classes, for example hepatitis B antibodies; and antigenic proteins such as insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), intrinsic factor, transcobalamin, enzymes such as alkaline phosphatase and lactic dehydrogenase, and hepatitis-associated antigens such as hepatitis B surface antigen (HB$_s$Ag), hepatitis e antigen (HB$_e$Ag) and hepatitis core antigen (HB$_c$Ag). Representative of polypeptide ligands are angiotensin I and II, C-peptide, oxytocin, vasopressin, neurophysin, gastrin, secretin, and glucagon.

Since, as peptides, ligands of this general category possess numerous available carboxylic acid and amino groups, coupling to the amino-derivative of the chemiluminescent label can proceed according to conventional peptide condensation reactions such the carbodiimide reaction, the mixed anhydride reaction, and so forth as described hereinabove, or by the use of conventional bifunctional reagents capable of coupling carboxylic acid or amino functions to the amino group in the label derivative as likewise described above. General references concerning the coupling of proteins to primary amines or carboxylic acids are mentioned in detail above.

Haptens

Haptens, as a class, offer a wide variety of organic substances which evoke an immunochemical response in a host animal only when injected in the form of an immunogen conjugate comprising the hapten coupled to a carrier molecule, almost always a protein such as albumin. The coupling reactions for forming the immunogen conjugates are well developed in the art and in general comprise the coupling of a carboxylic acid ligand or a carboxylic acid derivative of the ligand to available amino groups on the protein carrier by formation of an amide bond. Such well known coupling reactions are directly analogous to the present formation of labeled conjugates by coupling carboxylic acid ligands or binding analogs to the amino-derivative of the chemiluminescent label.

Hapten ligands which themselves contain carboxylic acid functions, and which thereby can be coupled directly to the amino-derivative of the label, include the iodothyronine hormones such as thyroxine and liothyronine, as well as other materials such as biotin, valproic acid, folic acid and certain prostaglandins. Following are representative synthetic routes for preparing carboxylic acid binding analogs of hapten ligands which themselves do not contain an available carboxylic acid function whereby such analogs can be coupled to the amino-derivative of the label by the aforementioned peptide condensation reactions or bifunctional coupling agent reactions (in the structural formulae below, n represents an integer, usually 1 through 6).

Carbamazepine

Dibenz[b,f]azepine is treated sequentially with phosgene, an ω-aminoalkanol, and Jones reagent (chromium trioxide in sulfuric acid) according to the method of Singh, U.S. Pat. No. 4,058,511 to yield the following series of carboxylic acids:

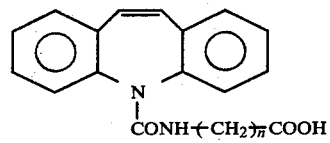

Quinidine

Following the method of Cook et al, *Pharmacologist* 17:219(1975), quinidine is demethylated and treated with 5-bromovalerate followed by acid hydrolysis to yield a suitable carboxylic acid derivative.

Digoxin and Digitoxin

The aglycone of the cardiac glycoside is treated with succinic anhydride and pyridine according to the method of Oliver et al, *J. Clin. Invest.* 47:1035(1968) to yield the following:

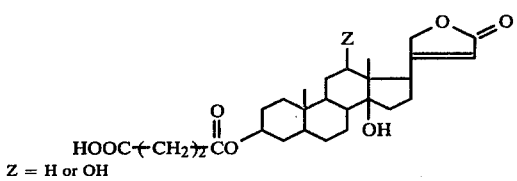

Z = H or OH

Theophylline

Following the method of Cook et al, *Res. Comm. Chem. Path. Pharm.* 13:497(1976), 4,5-diamino-1,3- dimethylpyrimidine-2,6-dione is heated with glutaric anhydride to yield the following:

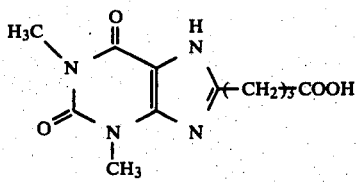

CL Phenobarbital and Primidone

Sodium phenobarbital is heated with methyl 5-bromovalerate and the product hydrolyzed to the corresponding acid derivative of phenobarbital [Cook et al, *Quantitative Analytic Studies in Epilepsy*, ed. Kelleway and Peterson, Raven Press (New York 1976) pp. 39–58]:

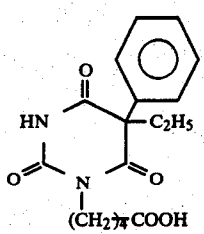

To obtain the acid derivative of primidone following the same Cook et al reference method, 2-thiophenobarbital is alkylated, hydrolyzed, and the product treated with Raney nickel to yield:

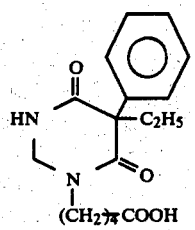

Diphenylhydantoin

Following the method of Cook et al, *Res. Comm. Chem. Path. Pharm.* 5:767(1973), sodium diphenylhydantoin is reacted with methyl 5-bromovalerate followed by acid hydrolysis to yield the following:

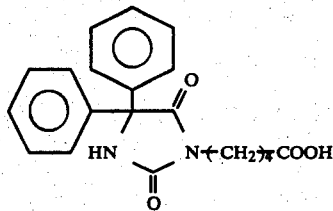

Morphine

Morphine free base is treated with sodium β-chloroacetate according to the method of Spector et al, *Science* 168:1347(1970) to yield a suitable carboxylic acid derivative.

Nicotine

According to the method of Langone et al, *Biochem.* 12(24):5025(1973), trans-hydroxymethylnicotine and succinic anhydride are reacted to yield the following:

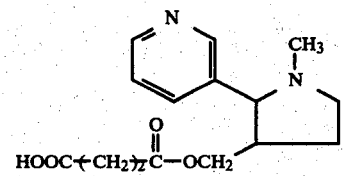

Androgens

Suitable carboxylic acid derivatives of testosterone and androstenedione linked through either the 1- or 7-position on the steroid nucleus are prepared according to the method of Bauminger et al, *J. Steroid Biochem.* 5:739(1974). Following are representative testosterone derivatives:

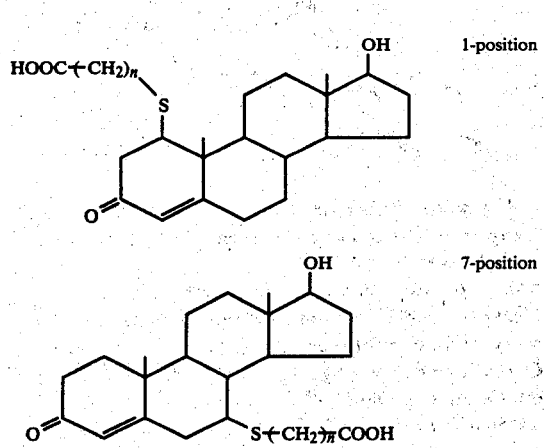

Estrogens

Suitable carboxylic acid derivatives of estrogens, e.g., estrone, estradiol and estriol, are prepared according to the method of Bauminger et al, supra, as represented by the following estrone derivative:

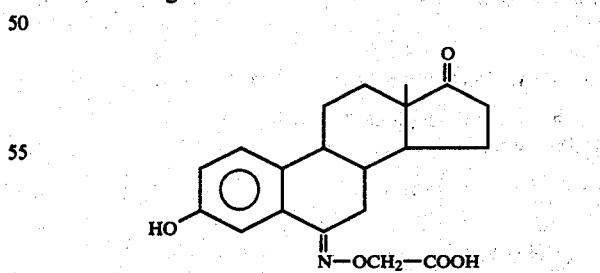

Progesterones

Suitable carboxylic acid derivatives of progesterone and its metabolites linked through any of the 3-, 6- or 7-positions on the steroid nucleus are prepared according to the method of Bauminger et al, supra, as represented by the following progesterone derivatives:

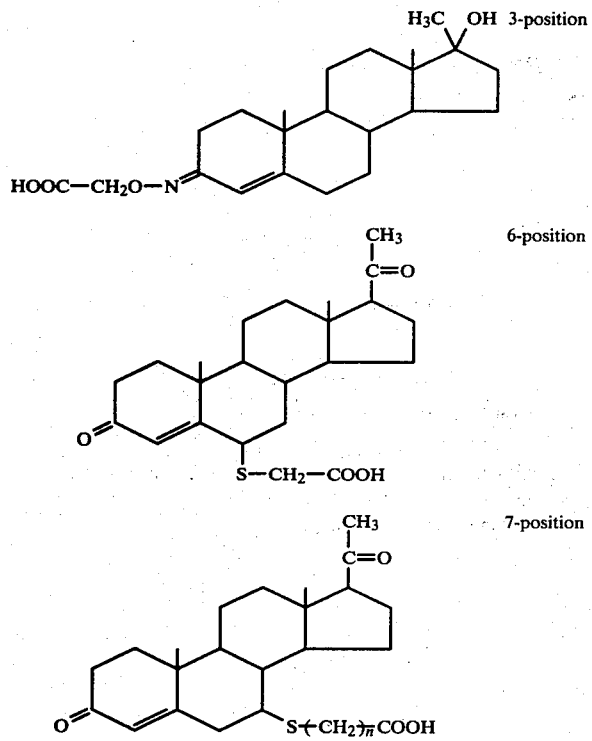

The methods described above are but examples of the many known techniques for forming suitable carboxylic acid derivatives of haptens of analytical interest. The principal derivation techniques are discussed in *Clin. Chem.* 22:726(1976) and include esterification of a primary alcohol with succinic anhydride [Abraham and Grover, *Principles of Competitive Protein-Binding Assays*, ed. Odell and Daughaday, J. B. Lippincott Co. (Philadelphia 1971) pp. 140-157], formation of an oxime from reaction of a ketone group with carboxylmethyl hydroxylamine [*J. Biol. Chem.* 234:1090(1959)], introduction of a carboxyl group into a phenolic residue using chloroacetate [*Science* 168:1347(1970)], and coupling to diazotized p-aminobenzoic acid in the manner described in *J. Biol. Chem.* 235:1051(1960).

The present invention will now be illustrated, but is not intended to be limited, by the following Examples:

Biotin Conjugate

A. Preparation of the Labeled Conjugate

The reaction sequence for this synthesis is described and shown schematically in *Anal. Chem.* 48:1933(1976).

4-(3-Chloro-2-hydroxypropylamino)-N-methylphthalimide

Twenty-five grams (g) (0.142 mole) 4-amino-N-methylphthalimide [Flitsch, *Chem. Ber.* 94:2494(1961)] and 20.7 g (0.21 mole) 1-chloro-2,3-epoxypropane were added to 150 ml 2,2,2-trifluoroethanol and the reaction mixture was heated to reflux with stirring for 48 hours. Seventy to eighty ml of 2,2,2-trifluoroethanol was removed by distillation and a heavy yellow precipitate formed when the remaining solution cooled to room temperature. This precipitate was triturated with ethyl acetate, collected by filtration and dried to give 29.5 g (77% yield) of the desired phthalimide intermediate m.p. 136°-138.5° C.

Analysis: Calculated for $C_{12}H_{13}ClN_2O_3$: C, 53.64; H, 4.88; N, 10.45. Found: C, 53.87; H, 4.85; N, 10.81.

4-[3-(N-Phthalamido)-2-hydroxypropylamino]-N-methylphthalimide

The phthalimide intermediate prepared above (13.5 g, 0.05 mole) and 15.7 g (0.085 mole) potassium phthalimide were heated to reflux with stirring in 150 ml dimethylformamide for 24 hours. The dimethylformamide was removed and the residue was washed with water and filtered. The yellow filter cake was recrystallized from acetic acid-water to give 12.8 g (67% yield) of the bis-phthalimide intermediate, m.p. 247°-248.5° C.

Analysis: Calculated for $C_{20}H_{17}N_3O_5$: C, 63.32; H, 4.52; N, 11.08. Found: C, 63.16; H, 4.38; N, 10.93.

6-(3-Amino-2-hydroxypropylamino)-2,3-dihydrophthalazine-1,4-dione

The bis-phthalimide intermediate from above (5.0 g, 13.2 mmole), 90 ml absolute ethanol and 35 ml 95% hydrazine were refluxed with stirring for 4 hours. The solvent was removed under a vacuum and the resulting solid was dried for 24 hours under vacuum at 120° C. This material was stirred for 1 hour with 70 ml of 0.1 N hydrochloric acid. The insoluble material was removed by filtration and the filtrate was adjusted to pH 6.5 with saturated sodium bicarbonate. The white precipitate which formed was collected by filtration and dried to give 2.2 g of the product (67% yield). After recrystallization from water, the compound decomposed at 273° C.

Analysis: Calculated for $C_{11}H_{14}N_2O_3$: C, 52.79; H, 5.64; N, 22.39. Found: C, 52.73; H, 5.72; N, 22.54.

The efficiency of the amino-derivative (i.e., the label derivative) in a chemiluminescent reaction and the detection limit of such derivative were determined as follows.

In determining efficiency, the label derivative and luminol (5-amino-2,3-dihydrophthalazine-1,4-dione) were oxidized individually at several levels in the picomolar range and related to the peak light intensities generated by a graph plot. Linear portions of the resulting curves allowed calculation of change in peak light intensity per unit concentration for the label derivative and for luminol. Efficiency of the label derivative was expressed as a percentage of the slope produced with luminol.

Reaction mixtures (150 μl) of the following composition were assembled in 6×50 mm test tubes mounted in a Dupont 760 Luminescence Biometer (E. I. duPont de Nemours and Co., Wilmington, Del. USA) with a sensitivity setting of 820:50 mM sodium hydroxide, 0.07 μM hematin (Sigma Chemical Co., St. Louis, Mo. USA) and either the amino-derivative or luminol at varying concentrations in the picomolar (pM) range (diluted with $H_2O$ from a 1 mM stock solution in 0.1 M sodium carbonate, pH 10.5). Each mixture was incubated 10 minutes at room temperature and 10 μl of 90 mM hydrogen peroxide was added to initiate the chemiluminescent reaction. Peak light intensity values were recorded from the instrument readings. All reactions were performed in triplicate and averaged. The efficiency of the label derivative was found to be 10%.

Detection limit was defined as the concentration of the label derivative that produced a peak light intensity one and a half times the background chemiluminescence in the reaction mixture. The detection limit for the label derivative was found to be 20 pM.

The N-ethylated derivative, 6-[N-(3-amino-2-hydroxypropyl)-N-ethylamino]-2,3-dihydrophthalazine-1,4-dione, of the above-described amino-derivative was also prepared by treating 4-amino-N-methylphthalimide with diethyl sulfate under reflux in 2,2,2-trifluoroethanol and then following the same synthesis as described above to convert the N-ethylated intermediate through the phthalimide and bis-phthalimide intermediate stages to the N-ethylated amino-derivative. The efficiency of this compound in the hematin catalyzed chemiluminescent reaction was found to be 46% and the detection limit 5 pM.

6-(3-Biotinylamido-2-hydroxypropylamino)-2,3-dihydrophthalazine-1,4-dione [biotin-isoluminol conjugate]

Biotin (0.29 g, 1.2 mmole) and 0.17 ml triethylamine were dissolved in 20 ml dry dimethylformamide under anhydrous conditions and cooled to −10° C. A solution of 0.141 ml ethyl chloroformate in 2.86 ml ether was added slowly and the reaction was stirred for 30 minutes. A precipitate which formed was separated by filtration. A suspension consisting of 600 mg (2.4 mmole) of the amino-derivative intermediate from above, 20 ml dry dimethylformamide and 1 ml dry pyridine was added to the filtrate quickly. This mixture was stirred at −10° C. for 30 minutes and then at room temperature overnight. During this period a solution was obtained. The dimethylformamide was removed by distillation at 60° C. and 0.10 mm Hg pressure. The oily residue was stirred with 50 ml of 0.1 N hydrochloric acid for 1 hour. A white solid which formed was filtered and washed with 0.1 N hydrochloric acid and then water. After drying under a vacuum at room temperature overnight, 0.55 g (97% yield) of the labeled conjugate was obtained, m.p. 170°-3° C.

Analysis: Calculated for $C_{21}H_{28}N_6O_5S$: C, 52.92; H, 5.92; N, 17.64.

Found: C, 51.69; H, 5.90; N, 17.63.

B. Binding Assays for Biotin and Avidin Using Enzyme Catalyzed Monitoring Reaction The chemiluminescent reaction system used in this example was based on the following reaction:

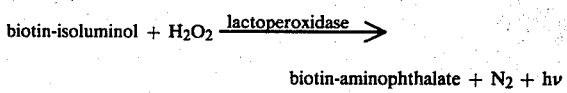

biotin-isoluminol + $H_2O_2$ $\xrightarrow{\text{lactoperoxidase}}$ biotin-aminophthalate + $N_2$ + hν

Nine specific binding reaction mixtures were prepared, each having a total volume of 140 μl and each containing 0.1 M tris-(hydroxymethyl)-aminomethane hydrochloride buffer (Tris-HCl) at pH 7.4 and biotin, biotin-isoluminol labeled conjugate (prepared as above), and avidin (added last) in the concentrations indicated in Table 1. After 5 minute incubation at 25° C., 10 μl 0.1 M Tris-HCl buffer at pH 7.4 containing 20 units/ml lactoperoxidase [Sigma Chemical Co., St. Louis, Mo. USA; assayed as described in Methods in Enzymology XVIIA, (1970) p. 653-Assay 2] was added to each reaction mixture. After incubation at 25° C. for 2 additional minutes, 10 μl of 0.95 mM hydrogen peroxide in 10 mM Tris-HCl buffer at pH 7.4 was injected into each reaction mixture and the peak light intensity produced in each was measured using the Dupont Model 760 Bioluminescence Photometer. The results appear in Table 1.

TABLE 1

| reaction mixture | concentration of biotin (μM) | concentration of biotin-isoluminol conjugate (nM) | concentration of avidin (units/ml) | peak light intensity |
|---|---|---|---|---|
| 1 | — | — | — | 0.8 |
| 2 | — | — | 0.14 | 0.9 |
| 3 | — | 84 | — | 1.9 |
| 4 | — | 84 | 0.14 | 25.3 |
| 5 | 4 | — | — | 0.8 |
| 6 | 4 | 84 | — | 2.2 |
| 7 | 4 | — | 0.14 | 0.9 |
| 8 | 4 | 84 | 0.14 | 6.1 |
| 9 | 1.3 | 84 | 0.14 | 10.4 |

Reactions 1,2,5 and 7 were controls and show that in the absence of biotin-isoluminol conjugate, only a low background amount of light was measured. The result of reactions 3 and 6 indicate that the biotin-isoluminol conjugate was active in the chemiluminescent reaction and that the presence of free biotin had no significant effect on such activity. The result of reaction 4 shows that in the presence of avidin, a binder for biotin, the activity of the biotin-isoluminol conjugate increased. This result is rather unexpected since one would anticipate that binding of avidin to the conjugate should limit the availability of the isoluminol moiety for the chemiluminescent reaction. The reason for the observed enhancement of light-production is not understood. A comparison of the results of reactions 4,8, and 9 demonstrate that the enhancement of light production is decreased inversely with the amount of free biotin present.

This example demonstrates that the ligands avidin and biotin can be determined using the present labeled conjugates and that according to the present invention the effect of binding between the labeling substance in the conjugate and a corresponding binding partner may be an enhancement, rather than inhibition, of the activity of the labeling substance.

A further experiment was conducted using the same lactoperoxidase-catalyzed monitoring reaction.

Six specific binding reaction mixtures were prepared, each having a total volume of 140 μl and each containing 0.1 M Tris-HCl buffer at pH 7.4, 84 nM biotin-luminol conjugate (prepared as above), biotin at the concentrations indicated in Table 2, and 0.035 units/ml avidin (added last). After a 5 minute incubation at 25° C., 10 μl of lactoperoxidase (20 units/ml) were added to each reaction mixture.

After an additional 2 minute incubation, 10 μl 0.95 mM hydrogen peroxide in 10 mM Tris-HCl buffer at pH 7.4 was injected into each reaction mixture and the peak light intensity produced in each was measured as in the previous experiment. The results appear in Table 2.

TABLE 2

| reaction mixture | concentration of biotin (nM) | peak light intensity |
|---|---|---|
| 1 | 0 | 23.5 |
| 2 | 67 | 21.1 |
| 3 | 134 | 15.5 |
| 4 | 200 | 12.6 |
| 5 | 268 | 12.3 |
| 6 | 400 | 8.1 |

It was thus demonstrated that the magnitude of the peak light intensity produced by the chemiluminescent reaction system was an inverse function of the amount of biotin present in the specific binding reaction mixture. The present invention therefore provides labeled conjugates useful for determining the presence of ligands in a liquid medium.

C. Binding Assay for Biotin Using Non-Enzymatic Monitoring Reaction

The chemiluminescent reaction system used in this example was based on the following reaction:

biotin-isoluminol + $KO_2$ → biotin-aminoph-thalate + $N_2$ + $h\nu$

Sixteen specific binding reaction mixtures were prepared, each having a total volume of 150 μl and each containing 0.1 M Tris-HCl at pH 8.0, 42 nM biotin-isoluminol conjugate (prepared as above), biotin at the concentrations indicated in Table 3, and 0.12 units/ml avidin (added last). After incubation at 25° C. for 5 minutes, 10 μl of dimethylformamide containing 0.15 M potassium superoxide ($KO_2$) (Alpha Products, Beverly, Mass. USA) and 0.10 M 1,4,7,10,13,16-hexaoxacylcooctadecane (Aldrich Chemical Co., Milwaukee, Wis. USA) were injected into each reaction mixture and the peak light intensity produced in each was measured as in the previous experiments. The results appear in Table 3.

TABLE 3

| reaction mixture | concentration of biotin (nM) | peak light intensity |
|---|---|---|
| 1 | 0 | 38.5 |
| 2 | 13 | 38.5 |
| 3 | 27 | 34.3 |
| 4 | 40 | 36.1 |
| 5 | 53 | 35.2 |
| 6 | 67 | 36.2 |
| 7 | 101 | 34.0 |
| 8 | 133 | 31.7 |
| 9 | 166 | 29.1 |
| 10 | 200 | 24.2 |
| 11 | 267 | 22.8 |
| 12 | 333 | 20.5 |
| 13 | 400 | 13.4 |
| 14 | 534 | 8.6 |
| 15 | 667 | 8.3 |
| 16 | 800 | 7.0 |

It was demonstrated that the magnitude of the peak light intensity produced by the chemiluminescent reaction system was an inverse function of the amount of biotin present in the specific binding reaction mixture. The present invention therefore provides labeled conjugates useful for determining the presence of ligands in a liquid medium.

Thyroxine Conjugates

A. Preparation of Labeled Conjugates

Following are descriptions of the preparation of the labeled thyroxine conjugates 6-N-[2-hydroxy-3-(thyroxinylamido)propyl]amino-2,3-dihydrophthalazine-1,4-dione and 6-{N-ethyl-N-[2-hydroxy-3-(thyroxinylamido)propyl]amino}-2,3-dihydrophthalazine-1,4-dione. The reaction sequences for these syntheses are outlined in Tables 4 and 5.

N-Trifluoroacetylthyroxine (2)

A solution of 20 grams (g) [25.6 millimole (mmol)] of L-thyroxine (1) (Sigma Chemical Co., St. Louis, Mo. USA) in 240 milliliters (ml) of ethyl acetate containing 46 ml of trifluoroacetic acid and 7.6 ml of trifluoroacetic anhydride was stirred at 0° C. for one hour. Upon adding 200 ml of water ($H_2O$), a suspension formed that was saturated with sodium chloride. The organic phase was separated, washed with saturated aqueous sodium chloride solution, dried over anhydrous magnesium sulfate, filtered and evaporated. When dry, the crystalline residue amounted to 21.3 g of the N-protected thyroxine derivative (2). A sample was recrystallized from ether-pentane to give fine white crystals, melting point (m.p.) 233°–235° C. (decomposed).

Analysis: Calculated for $C_{17}H_{10}F_3I_4NO_5$: C, 23.39; H, 1.15; N 1.60. Found: C, 23.23; H, 1.12; N, 1.59.

Infrared Spectrum (KCl): 1700 cm$^{-1}$ (carbonyl).

Optical Rotation $[\alpha]_D^{25} = -14.97°$ (c 1.0, dimethylsulfoxide).

TABLE 4

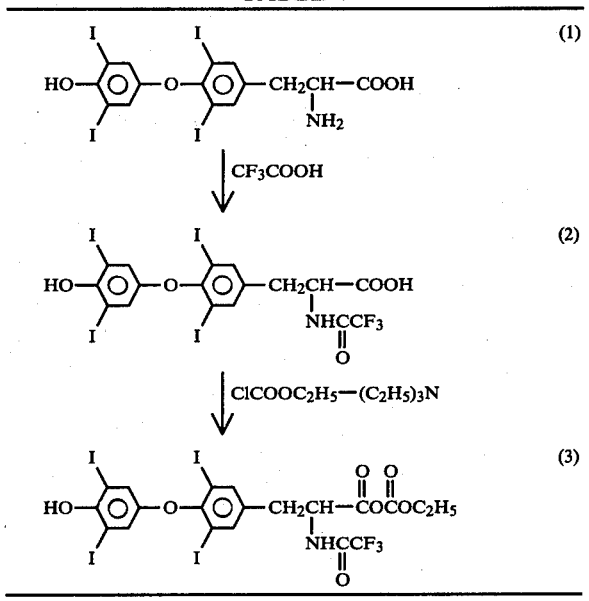

TABLE 5

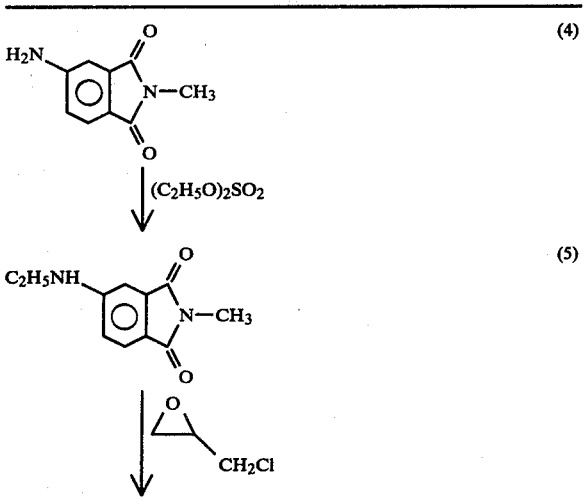

TABLE 5-continued

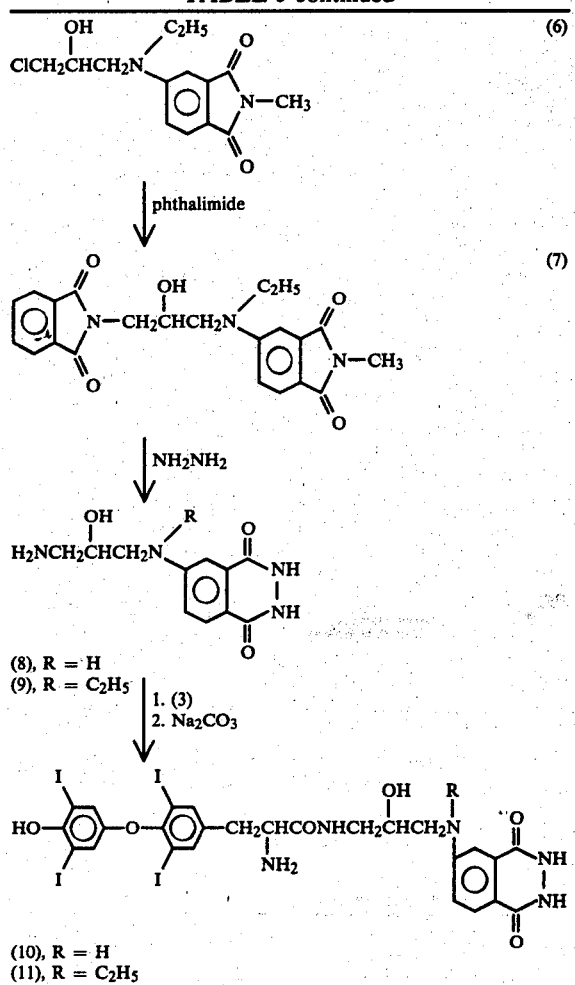

(8), R = H
(9), R = C₂H₅

N-Trifluoroacetylthyroxinyl Ethyl Carbonic Anhydride (3)

A mixture of 0.17 ml of triethylamine and 1.05 g (1.2 mmol) of N-trifluoroacetylthyroxine (2) was dissolved in 20 ml of dry dimethylformamide at −10° C. under anhydrous conditions [Knappe et al, Biochem. Z. 338:599(1963)]. To this was added a solution of 0.14 ml (1.2 mmol) of ethyl chloroformate in 2.9 ml of dry ether. After 30 minutes the precipitate of triethylammonium chloride was removed by filtration. The filtrate, now containing the anhydride (3), was used without isolation in the reaction described below to form labeled conjugate (10).

4-N-Ethylamino-N-methylphthalimide (5)

A mixture of 10 g (0.057 mol) of 4-amino-N-methylphthalimide (4) [Flitsch, Chem. Ber. 94:2494(1961)], 17.5 g (0.11 mol) of diethyl sulfate, and 100 ml of 2,2,2-trifluoroethanol was refluxed for one day. The reaction mixture was cooled, concentrated under reduced pressure, and the residue partitioned between 250 ml of ethyl acetate and 100 ml of saturated sodium bicarbonate solution containing 10 ml of triethylamine. The ethyl acetate phase was separated, washed with saturated aqueous sodium chloride solution, dried over anhydrous magnesium sulfate, filtered, and evaporated. The residue was recrystallized twice from acetone-hexane and then from aqueous methanol to give 3.4 g (29% yield) of the phthalimide (5) as fine yellow crystals, m.p. 157° C.

Analysis: Calculated for $C_{11}H_{12}N_2O_2$: C, 64.69; H, 5.92; N, 13.71. Found: C, 64.00; H, 5.71; N, 13.37.

NMR Spectrum ($C_5D_5N$): δ0.5 (t, J=7 Hz, 3H), 2.1 (s, 3H).

4-[N-(3-Chloro-2-hydroxypropyl)-N-ethylamino]-N-methylphthalimide (6)

A mixture of 3.1 g (15 mmol) of the phthalimide (5), 1.2 g (15 mmol) of 1-chloro-2,3-epoxypropane, and 30 ml of 2,2,2-trifluoroethanol was refluxed for 24 hours. At the end of this time, another 1.2 g of 1-chloro-2,3-epoxypropane was added. After heating for an additional 24 hours, the reaction was cooled and evaporated and the residue chromatographed on 150 g of silica gel 60 (E. Merck, Darmstadt, West Germany), eluting with a 9:1 mixture (v:v) of carbon tetrachloride and acetone. Fifteen ml fractions were collected. Fractions numbered 90 to 160 were combined and evaporated to give 3 g of a yellow-red oil. The oil was crystallized from acetone-hexane and recrystallized twice from aqueous methanol to give 1 g (22% yield) of the phthalimide (6) as fine yellow needles, m.p. 123° C.

Analysis: Calculated for $C_{14}H_{17}ClN_2O_3$: C, 56.66; H, 5.78; N, 9.44. Found: C, 56.50; H, 5.93; N, 9.26.

NMR Spectrum ($C_5D_5N$): δ0.65 (t, 3H, J=8 Hz), 2.6 (s, 3H).

4-{N-Ethyl-N-[2-hydroxy-3-(N-phthalimido)propyl]amino}-N-methylphthalimide (7)

A mixture of 25 g (0.08 mol) of the phthalimide (6), 23 g (0.13 mol) of potassium phthalimide, and 150 ml of dry dimethylformamide was refluxed for 36 hours. Removal of the solvent left a brown residue that was triturated with methanol to give 19 g of yellow solid. Recrystallization from aqueous acetic acid, then from aqueous methanol, gave 16 g (49% yield) of the bis-phthalimide (7) as a yellow solid, m.p. 158°–160° C.

Analysis: Calculated for $C_{22}H_{21}N_3O_5$: C, 64.85; H, 5.20; N, 10.31. Found: C, 64.81; H, 4.97; N, 10.54.

NMR Spectrum (d₆-DMSO): δ1.2 (t, 3H, J=6 Hz), 3.0 (s, 3H).

6-N-(3-Amino-2-hydroxypropyl)amino-2,3-dihydrophthalazine-1,4-dione (8)

This compound was prepared according to the method described both above relating to the biotin conjugate and in Anal. Chem. 48:1933(1976). As reported above, the efficiency of this amino-derivative (8) in the hematin catalyzed chemiluminescent reaction was 10% and the detection limit 20 pM.

6-[N-(3-Amino-2-hydroxypropyl)-N-ethyl]-2,3-dihydrophthalazine-1,4-dione (9)

A mixture of 15 g (0.037 mol) of the bis-phthalimide (7), 60 ml of 95% hydrazine, and 300 ml of absolute ethanol was refluxed for 3 hours. The reaction was cooled, evaporated to dryness, and the crystalline residue dried at 40° C./0.05 mm Hg overnight. The residue was then dried at 120° C./0.05 mm Hg for 4 hours. The resulting solid was stirred for 3 hours in dilute hydrochloric acid and filtered. When the pH of the filtrate was adjusted to 7.0, a precipitate formed amounting to 4.6 g (46% yield) of the amino-phthalhydrazide (9), m.p. 207°–210° C. (decomposed). A small sample was recrystallized from H$_2$O to give white crystals, m.p. 208°–211° C. (decomposed).

Analysis: Calculated for C$_{13}$H$_{18}$N$_4$O$_3$: C, 56.10; H, 6.52; N, 20.13. Found: C, 55.61; H, 6.50; N, 20.35.

The efficiency of the amino-derivative (9) and its detection limit were determined in the same manner as described above for the amino-derivative (8). The efficiency was formed to be 46% and the detection limit 5 pM.

6-N-[2-Hydroxy-3-(thyroxinylamido)propyl]amino-2,3-dihydrophthalazine-1,4-dione (10)

A suspension of 600 mg (2.4 mmol) of the amino-derivative (8) in 20 ml of dry dimethylformamide containing 1 ml of pyridine was stirred under argon for one hour. It was then drawn up into a syringe and added all at once to a −10° C. solution of 1.2 mmoles of N-trifluoroacetylthyroxinyl ethyl carbonic anhydride (3) in 20 ml of dimethylformamide. After stirring for 20 minutes at −10° C., the reaction was allowed to warm to room temperature and stirred overnight. Solvent was removed under high vacuum. The solid residue was stirred for 40 minutes in dilute hydrochloric acid, then filtered and drive under high vacuum to give 1.27 g of a free-flowing powder.

The trifluoroacetyl protecting group was removed by stirring 1.0 g of this powder for 5 hours in a methanol/H$_2$O solution. The pH of the solution was adjusted to 10.7 with solid sodium carbonate. The pH was reduced to 7.0 with hydrochloric acid and a white precipitate collected and dried. When dry this amounted to 700 mg (59% yield) of the labeled conjugate (10) as a yellowish-white powder, m.p. 235° C. (decomposed).

Analysis: Calculated for C$_{26}$H$_{23}$I$_4$N$_5$O$_6$: C, 30.95; H, 2.30; N, 6.94. Found: C, 30.17; H, 2.33; N, 6.33.

6-{N-Ethyl-N-[2-hydroxy-3-(thyroxinylamido)propyl]amino}-2,3-dihydrophthalazine-1,4-dione (11)

A solution of 1.06 g (1.2 mmol) of N-trifluoroacetylthyroxine (2) in 20 ml of dimethylformamide containing 0.17 ml of triethylamine was cooled to −10° C. To this was added 0.14 ml (1.2 mmol) of ethyl chloroformate. After 30 minutes at this temperature the solution, now containing the mixed anhydride (3), was filtered to remove precipitated triethylamine hydrochloride and added to a suspension of 668 mg (2.4 mmol) of the amino-derivative (9) in 20 ml of dimethylformamide. After stirring two days at room temperature, the solvent was removed under vacuum, and the residue washed with 10% hydrochloric acid, collected by filtration, and dried.

To remove the trifluoroacetyl blocking group, the solid was dissolved in 50 ml of 0.1 M sodium carbonate (pH 10.5) to which was added a small amount of dimethylformamide to achieve solution. After one day at room temperature, it was evaporated to dryness. The residue was taken up in 30 ml of H$_2$O, and the pH adjusted to 7.2 with dilute hydrochloric acid. A solid precipitated that was collected and dried at 60° C. under high vacuum to give 600 mg (50% yield) of the labeled conjugate (11) as white crystals, m.p. >240° C. (decomposed).

Analysis: Calculated for C$_{28}$H$_{27}$I$_4$N$_5$O$_6$: C, 32.42; H, 2.62; N, 6.75. Found: C, 29.81; H, 2.69; N, 5.45.

B. Binding Assay for Thyroxine

Competitive binding reaction mixtures (120 μl) were assembled in triplicate by combining the following reagents: 12 μl of 100 mM Tris-HCl (pH 8.8), 12 μl of 77 nM labeled conjugate (11) [labeled conjugate (10) could be used as well] in 10 mM Tris-HCl (pH 8.8), varying volumes of 40 nM thyroxine in the same buffer, 10 μl of a preparation of antibody to thyroxine in 5 mM phosphate buffer (pH 6.7), and a sufficient volume of H$_2$O to make a final volume of 120 μl. After a 1 hour incubation at room temperature, the free- and bound-species of the labeled conjugate were separated for each reaction mixture by applying a 100 μl aliquot to small columns (0.3 μl bed volume) of Sephadex G-25 (Pharmacia Fine Chemicals, Uppsala, Sweden) previously washed with 10 mM Tris-HCl (pH 8.8). The bound-species of the labeled conjugate was eluted from the column with 0.5 ml of the same buffer leaving the free-species in the column.

An aliquot (115 μl) of each column effluent was added to 35 μl of 0.29 μM hematin (Sigma Chemical Co., St. Louis, Mo., USA) and 214 mM sodium hydroxide in a 6×50 mm test tube. Each tube was placed in the Dupont 760 Biometer and 10 μl of 90 mM hydrogen peroxide in 10 mM Tris-HCl (pH 7.4) were added. The resulting peak intensity of the light produced in each chemiluminescent reaction was recorded from the instrument reading and the results from the triplicate runs were averaged.

The relationship of the amount of thyroxine in the binding reaction to peak light intensity is shown in Table 6 below.

TABLE 6

| volume of thyroxine solution added (μl) | peak light intensity |
| --- | --- |
| 0 | 13.8 |
| 12 | 13.5 |
| 48 | 3.5 |

The results demonstrate that the labeled conjugate of the present invention is useful in binding assays for determining a ligand in a liquid medium.

What is claimed is:

1. A compound of the formula:

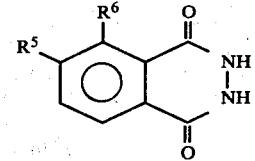

wherein one of R$^5$ and R$^6$ is hydrogen and the other is —NR$^7$R$^8$; R$^7$ is hydrogen or straight chain alkyl containing 1–4 carbon atoms and R$^8$ is

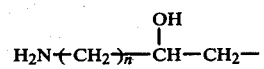

wherein n=1–3.

2. The compound of claim 1 wherein R$^5$ is —NR$^7$R$^8$.
3. The compound of claim 2 wherein n=1.
4. The compound of claim 3 wherein R$^7$ is hydrogen.
5. The compound of claim 3 wherein R$^7$ is ethyl.

* * * * *